(12) United States Patent  
Uchic et al.

(10) Patent No.: US 6,978,664 B1  
(45) Date of Patent: Dec. 27, 2005

(54) DUAL FUNCTION INDENTER

(75) Inventors: Michael Uchic, Centerville, OH (US);  
Dennis Dimiduk, Bellbrook, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 199 days.

(21) Appl. No.: 10/713,131

(22) Filed: Nov. 17, 2003

(51) Int. Cl.⁷ .............................................. G01N 3/34
(52) U.S. Cl. ........................................................ 73/85
(58) Field of Search ........................... 73/12.01, 12.04, 73/81, 82, 85, 818

(56) References Cited

U.S. PATENT DOCUMENTS

| | | | |
|---|---|---|---|
| 4,820,051 A * | 4/1989 | Yanagisawa et al. ....... 356/626 |
| 4,852,397 A | 8/1989 | Haggag | |
| 5,461,907 A * | 10/1995 | Tench et al. ................... 73/105 |
| 5,546,797 A * | 8/1996 | Dutta et al. ................ 73/150 A |
| 5,999,887 A | 12/1999 | Giannakopoulos et al. | |
| 6,301,956 B1 * | 10/2001 | Fujita et al. .................... 73/82 |
| 6,311,135 B1 * | 10/2001 | Suresh et al. .................. 702/43 |

* cited by examiner

*Primary Examiner*—Robert Raevis  
(74) *Attorney, Agent, or Firm*—AFMCLO/JAZ; Richard A. Lambert

(57) ABSTRACT

A dual function indenter for use in a nanoindentation system is disclosed. The indenter of the present invention includes an indentation tip having a machined flat at its distal end forming a compression platen. A sharp imaging probe tip adjacent the machined flat extends parallel to the centerline axis of the indentation tip. The sharp imaging probe tip extends beyond the surface of the machined flat for in situ scanning/imaging of the sample surface.

3 Claims, 3 Drawing Sheets

DUAL FUNCTION INDENTER

RIGHTS OF THE GOVERNMENT

The invention described herein may be manufactured and used by or for the Government of the United States for all governmental purposes without the payment of any royalty.

BACKGROUND OF THE INVENTION

The present invention relates generally to materials testing apparatuses, and more specifically, to an indenter for a nanoindentation instrument.

The use of penetration techniques to obtain information relating to the mechanical properties of a material sample is well known. Typically, an indenter having a indentation tip at the distal end is forced into a sample of a material and then extracted therefrom, leaving an indentation in the surface of the sample. Indicia pertaining to depth of penetration and force applied to the indenter are manipulated, typically by a dedicated computer, to determine material properties such as hardness or modulus of elasticity.

The testing of materials in this way can be readily performed in the nanoscale range through the use of several commercially available testing apparatuses. For example, MTS Systems Corporation, Eden Prairie, Minn. manufactures and sells a system for nanoindentation testing under the trademark Nano Indenter XP. Systems such as this one from MTS and others are quite effective at providing test results for small volumes of material (volume sizes less than 1000 cubic microns). Almost all nanoindentation systems use optical imaging to determine the location of the indentation test prior to testing, but this method is usually precise only to within a few microns. For ultra-precise positioning of the indentation tip within a few nanometers, some nanoindentation instruments (such as the Nano Indenter XP) can scan the indentation tip over the surface prior to testing, thereby creating a detailed image of the surface topology with nanometer-level resolution. This image can be subsequently used to precisely define the location for the indentation test.

These nanoindentation systems are not without their shortcomings, however, because the information gained from testing using a sharp indentation tip to penetrate a flat surface is generally limited to elastic modulus and hardness of the region tested. Information obtained from uniaxial compression experiments such as yield strength, ductility and work hardening would be desirable as well but can't be ascertained by traditional nanoindentation methods. Using micro-machining methods such as Focused Ion Beam machining, laser ablation, or Electrode Discharge Machining, compression samples with volume sizes less than 1000 cubic microns can be fabricated into the surface of a material and tested in uniaxial compression using the aforementioned commercial testing apparatuses. For uniaxial compression testing, the loading axis of the indenter tip must be positioned precisely parallel with the centerline of the compression specimen. If not, then bending moments may be applied to the test specimen that result in invalid test data. The requisite, precise placement of the indentation tip for uniaxial experiments using only an optical microscope is difficult or impracticable within the commercial nanoindentation apparatuses, but is easily achieved using the surface scanning/imaging method. However, these compression samples cannot be tested with a sharp tip, as the interpretation of the test data for a compression experiment relies on a uniform imposed stress state. A blunt or flat tip is used instead, but this prevents the use of the ultra-precise scanning/imaging technique, as the resolution of the system's scanning imaging capability is dependent on the shape of the indentation tip. As a result, the desirable uniaxial compression experiments have not been heretofore practicable.

A need exists therefore for an improved indenter tip for nanoindentation systems having a machined flat for uniaxial compression testing that can be precisely positioned. Such a tip would provide the dual in situ functionality of uniaxial compression loading and scanning/imaging of the sample surface.

SUMMARY OF THE INVENTION

Accordingly, it is a primary object of the present invention to provide an improved indenter for nanoindentation systems having an indentation tip including a machined flat for uniaxial compression testing that can be precisely positioned.

Another object of the present invention is to provide a dual function indenter enabling uniaxial compression loading as well as enabling scanning/imaging of the sample surface.

Yet another object of the present invention is to provide a dual function indenter enabling uniaxial compression loading as well as enabling scanning/imaging of the sample surface that can be effectively utilized within existing commercial nanoindentation systems.

These and other objects of the invention will become apparent as the description of the representative embodiments proceeds.

In accordance with the foregoing principles and objects of the invention, a dual function indenter for use in a nanoindentation system is disclosed. The indenter of the present invention includes an indentation tip having a machined flat at the distal end for use as a compression platen and a sharp imaging probe tip adjacent the machined flat and parallel to the centerline axis of the indentation tip. The sharp imaging probe tip extends beyond the surface of the machined flat and is used for in situ scanning/imaging of the sample surface. This enables an identification of the exact location of the indentation tip relative to the test sample. The combination of the machined flat compression platen and the sharp probe provides accurate mechanical loading of micromachined samples since the location of the test sample can be imaged and aligned with the loading axis of the nanoindentation system.

BRIEF DESCRIPTION OF THE DRAWING

The accompanying drawing incorporated in and forming a part of the specification, illustrates several aspects of the present invention and together with the description serves to explain the principles of the invention. In the drawing.

DETAILED DESCRIPTION OF THE INVENTION

Figure 1:
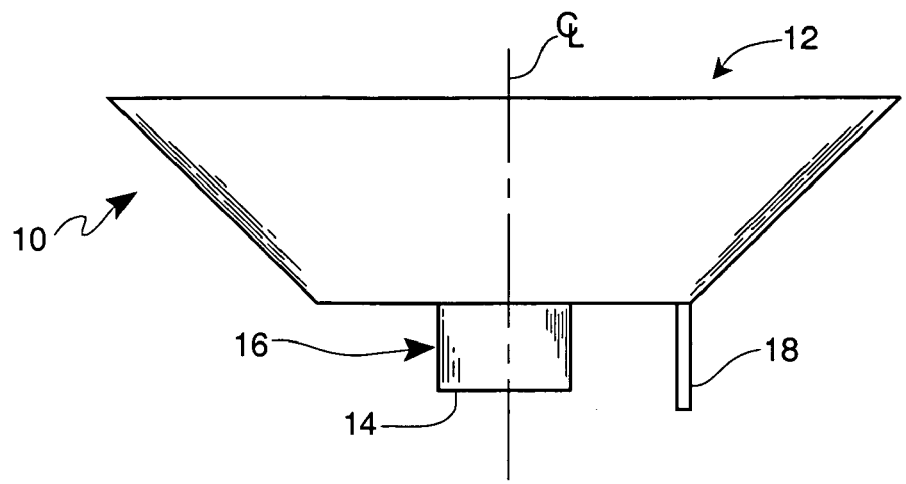
FIG. 1 is an elevational view of the dual function indenter of the present invention.

Reference is made to the drawing figures illustrating the dual function indenter 10 of the present invention. Advantageously, the indenter 10 enables uniaxial compression loading experiments on a nano scale as well as enabling scanning/imaging of the sample surface. It is another advantage of the present invention that the dual function indenter 10 can be used satisfactorily in the commercially available nano indentation systems such as, for example, the system sold under the trademark Nano Indenter XP, from MTS Systems Corporation, Eden Prairie, Minn. Note that other than the micro-featured distal end of the dual function indentation tip, the remainder of the tip can be identical to other indentation tips, which eliminates the need for specialized fitments to use the dual function tip in commercial systems.

Figure 2:
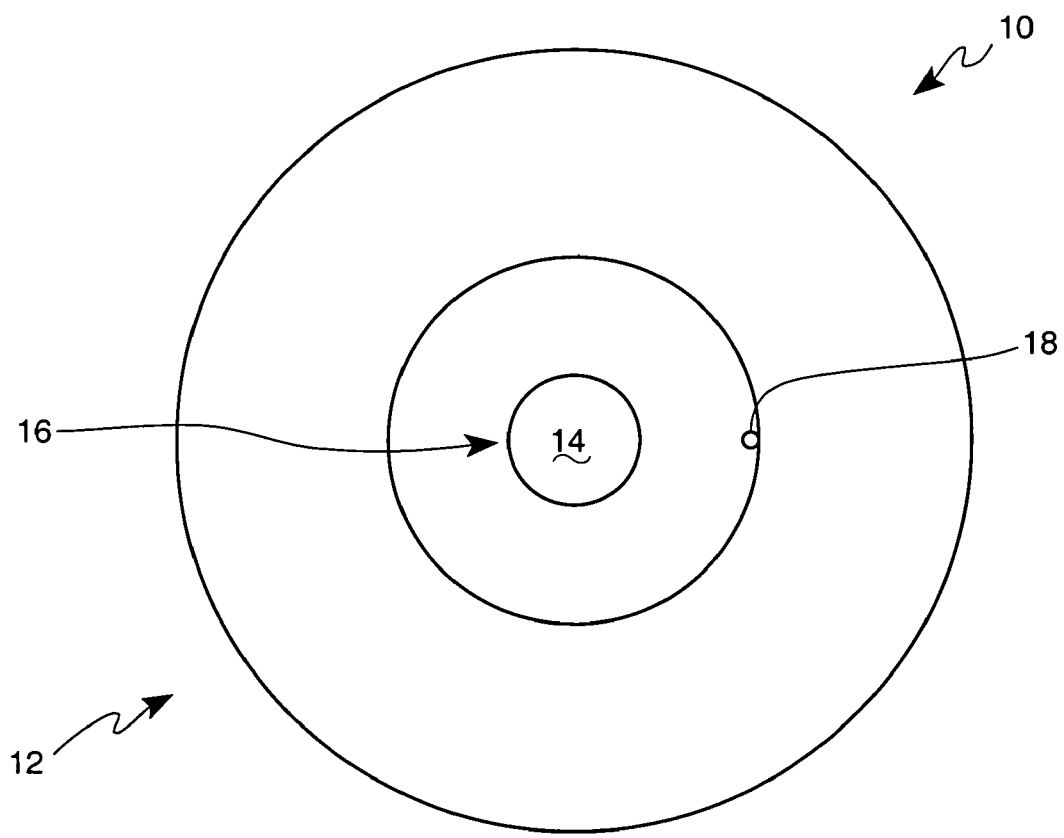
FIG. 2 is a plan view of the indentation tip of FIG. 1 viewed along the centerline axis toward the indentation tip.

As shown in FIGS. 1 and 2, the indenter 10 includes an indentation tip 12. A machined flat 14 is located on the distal end of the indentation tip 12 aligned perpendicularly to the centerline of the indention tip. The machined flat 14 forms a compression platen 16. As can be seen, the compression platen 16 extends away from the distal end of the indenter 10 along the centerline.

Advantageously and according to an important aspect of the present invention, the indenter 10 includes a sharp imaging probe tip 18 adjacent the machined flat 14, parallel to the centerline of the indentation tip 12. The sharp imaging probe tip 18 is provided for in situ scanning/imaging of the sample surface. This enables an identification of the exact location of the compression platen 16 relative to the test sample facilitating precise placement thereof. The combination of the machined flat 14 and the sharp probe 18 allows for accurate mechanical loading of micromachined samples since the location of the test sample can be imaged and aligned with the loading axis of the nanoindentation system. These unique features of the indenter 10 can be readily formed by the use of a Focused Ion Beam. Thus the indenter can be chosen from commercially available conical tips and machined accordingly.

Figure 5:
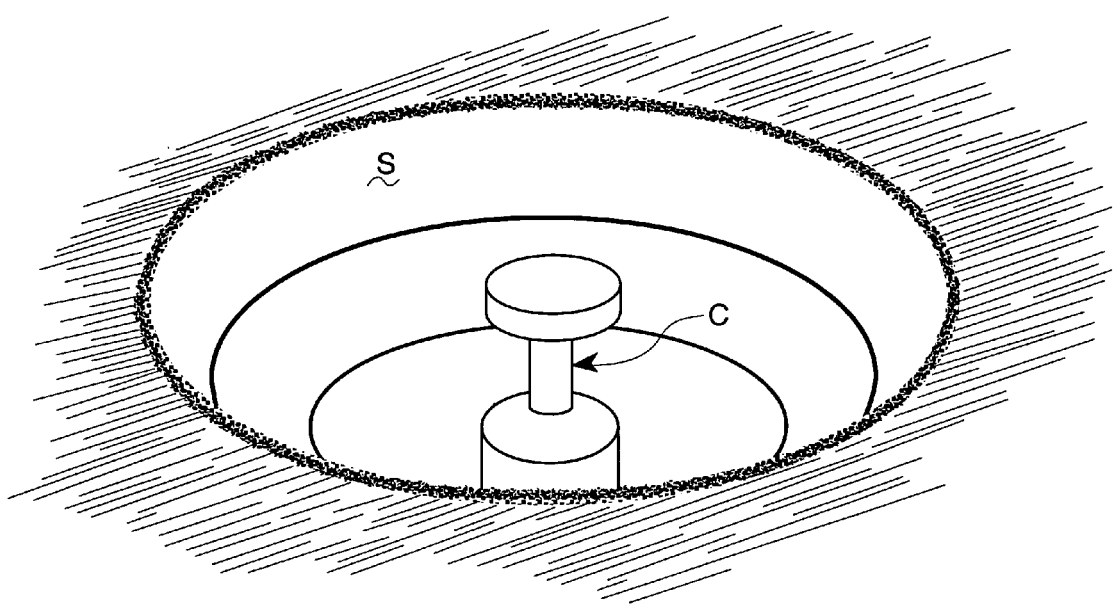
FIG. 5 is a diagrammatic view of a representative micron size compression sample for uniaxial compression experiments.

Reference is made to FIG. 5 wherein a representative micro-machined sample S fabricated for uniaxial compression testing is shown. In this example, a compression specimen generally designated C is machined into the sample. This can be done by Focused Ion Beam or other suitable technique. As can be perceived, an indenter must be precisely positioned along the centerline of the compression specimen C in order to return accurate test results. And conversely, if not precisely positioned with respect to the centerline of the compression specimen C, bending moments will be imparted upon compression, which give inaccurate results.

The sharp imaging probe tip 18 advantageously provides a means by which the position of the compression platen 16 can be accurately determined and positioned. Specifically, the sharp imaging probe tip 18 is parallel to the centerline of the compression platen 16, and is spaced at a known distance, far enough so as not to interfere with the mechanical loading. The indentation tip 12 is scanned over the surface to determine a topological image of the local surface area. In the Nano Indenter XP, this is accomplished by having the sharp imaging probe tip 18 maintain continuity with the surface by applying and maintaining a small but constant load through the tip. A piezoelectric stage moves the sample in a plane perpendicular to the centerline of the indentation tip 12, and the indentation tip 12 is free to move parallel to its centerline. The relative position of the piezoelectric stage and the relative displacement of the indentation tip 12 along its centerline are output to a dedicated computer (not shown), and systematic movement of the piezoelectric stage over an area allows for the creation of topological map with nanometer resolution in all directions. Thus, the location of the sharp imaging probe tip 18 with respect to the sample is determined, and the location of the centerline of the compression platen 16 with respect to the sample is readily calculated. The sharp imaging probe tip 18 enables accurate imaging, something not possible by viewing through the compression platen 16 alone.

Figure 3:
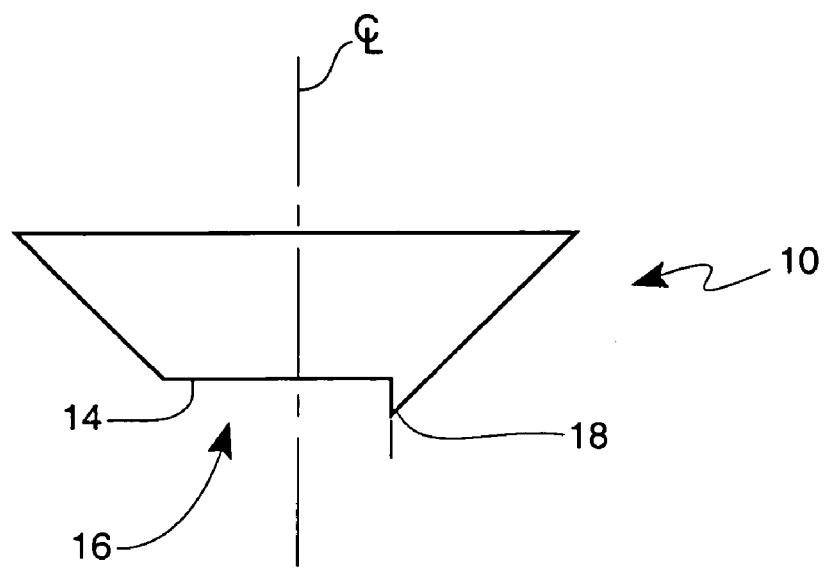
FIG. 3 is an elevational view of alternative embodiment of the dual function indenter of the present invention.
Figure 4:
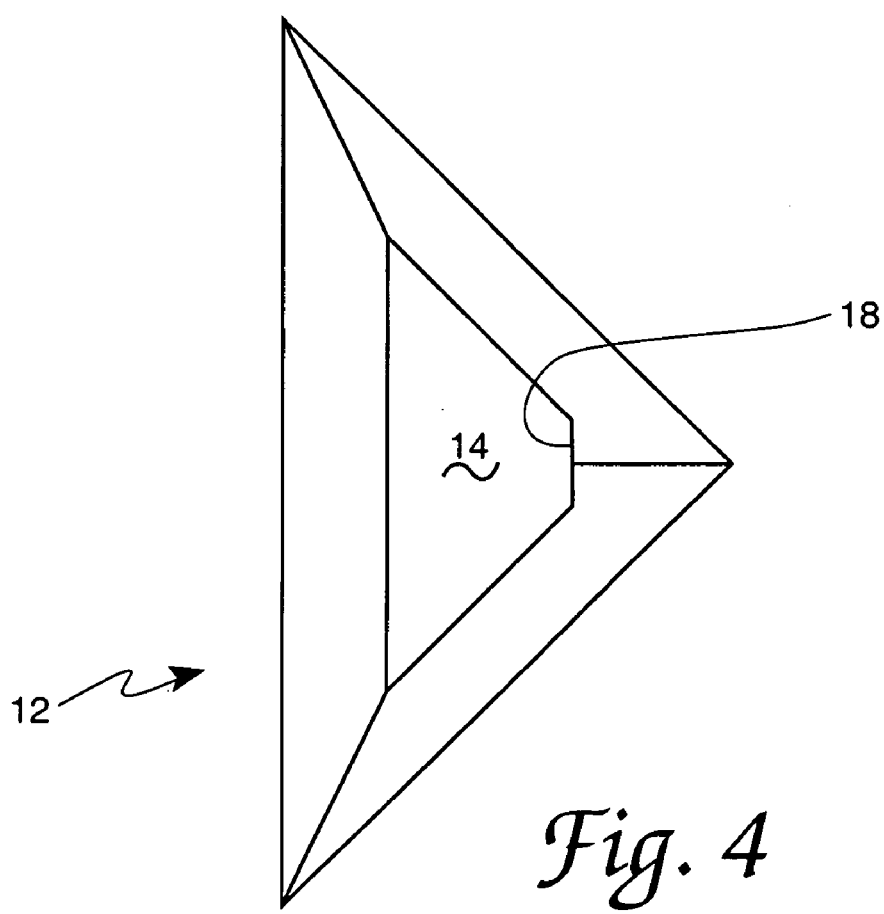
FIG. 4 is a plan view of the indentation tip of FIG. 3 viewed along the centerline axis toward the indentation tip.

Reference is now made to FIGS. 3 and 4 showing an alternative embodiment of the dual function indenter of the present invention. In this embodiment, the common Berkovich three sided pyramidal tip is machined by Focused Ion Beam into a machined flat 14 to form the compression platen 16. One. of the edges is allowed to remain to form the sharp imaging probe tip 18. Again, the sharp imaging probe tip 18 can be utilized to provide exact placement information concerning its location relative to the compression specimen C. Once the location is determined, the compression platen 16 is utilized to perform the desired compression experiments. Advantageously, the dual function indenter 10 of the present invention can be formed on any type of nanoindentation tip such as, Berkovich as illustrated above, pyramidal, cube corner and conical.

In summary, numerous benefits have been described from utilizing the principles of the present invention. The dual function indenter 10 of the present invention includes a machined flat 14 on the distal end forming a compression platen 16. A sharp imaging probe tip 18 also extends from the distal end parallel to the centerline of the indentation tip 12. The imaging probe 18 is utilized to provide location information of the compression platen 16 relative to the sample, enabling precise placement thereof, facilitating accurate compression testing of the sample.

The foregoing description of the preferred embodiment has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the inventions in various embodiments and with various modifications as are suited to the particular scope of the invention as determined by the appended claims when interpreted in accordance with the breadth to which they are fairly, legally and equitably entitled.

We claim:

1. An indenter for a nanoindentation instrument, comprising:
   an indentation tip having a centerline and a distal end;
   a flat on the distal end of said indentation tip, said flat being substantially perpendicular to said indentation tip centerline; and,
   an imaging probe extending from said indentation tip, said imaging probe being disposed substantially parallel to said indentation tip centerline and spaced a distance therefrom.

2. An indenter for a nanoindentation instrument, comprising:
   an indentation tip having a centerline and a distal end;

a flat on the distal end of said indentation tip, said flat being substantially perpendicular to said indentation tip centerline; and, an imaging probe extending from said indentation tip, said imaging probe being disposed substantially parallel to said indentation tip centerline and spaced a distance therefrom, said imaging probe extending beyond said flat.

3. An indenter for a nanoindentation instrument, comprising:

an indentation tip having a centerline and a distal end;

a flat on the distal end of said indentation tip, said flat being substantially perpendicular to said indentation tip centerline, said flat forming a compression platen; and, an imaging probe extending from said distal end of said indentation tip, said imaging probe being disposed substantially parallel to said indentation tip centerline and spaced a distance therefrom.

* * * * *